United States Patent
He et al.

(10) Patent No.: US 8,287,450 B1
(45) Date of Patent: Oct. 16, 2012

(54) LARYNGOSCOPE WITH EASY SWITCH-AND-SELECT 2-BLADES COMBINATION

(76) Inventors: KongYuan He, Encino, CA (US); Fanping Wang, Encino, CA (US)

( * ) Notice: Subject to any disclaimer, the term of this patent is extended or adjusted under 35 U.S.C. 154(b) by 0 days.

(21) Appl. No.: 13/302,155

(22) Filed: Nov. 22, 2011

(51) Int. Cl.
*A61B 1/267* (2006.01)
(52) U.S. Cl. .......................... 600/197; 600/193
(58) Field of Classification Search ............... 600/185, 600/190, 193, 197, 199; 206/363
See application file for complete search history.

(56) References Cited

U.S. PATENT DOCUMENTS

| 2,289,226 | A * | 7/1942 | Von Foregger | 600/193 |
| 7,695,433 | B2 * | 4/2010 | Simons | 600/186 |
| 2010/0179387 | A1 * | 7/2010 | Bird | 600/193 |

* cited by examiner

*Primary Examiner* — Eduardo C Robert
*Assistant Examiner* — David Comstock
(74) *Attorney, Agent, or Firm* — Jen-Feng Lee, Esq.

(57) ABSTRACT

The present invention relates to a laryngoscope having two selectable blades, straight and curved, foldable to the side grooves of a handle piece, so that doctors/nurses can react to the need to handle tracheal intubation for different patients, resulting in better airway management tasks. A battery compartment is made inside the body of the handle, providing a battery power source for optional LED lighting, or other type of lighting.

6 Claims, 4 Drawing Sheets

US 8,287,450 B1

LARYNGOSCOPE WITH EASY SWITCH-AND-SELECT 2-BLADES COMBINATION

FIELD AND BACKGROUND OF THE INVENTION

The present invention relates to an improved design for the medical instrument of laryngoscope where the 2-blade combination provides the enhanced flexibility of easy switch and select between the two blades, resulting in substantial benefits for patients in need of endotracheal intubation when physicians and nurses are constantly faced with the constraints of limited time and space, in non-optimized conditions.

A laryngoscope is used to assist in the opening up of a patient's airway, to facilitate the insertion of an endotracheal tube through the mouth and throat and into the trachea of a patient. Such laryngoscope typically includes a straight blade (generally known as the Miller type), or a curved blade (generally known as the Macintosh type), mounted on a handle portion. The blade, containing a flange portion, is used to expose the larynx and to allow insertion of the endotracheal tube into the trachea for proper tracheal intubation.

To cope with the varied anatomy of patients in need of tracheal intubation, the two types of blades work differently: the straight blade has a smaller displacement volume and will reach and lift the epiglottis directly; the curved blade has larger displacement volume and will be inserted between the epiglottis and base of the tongue.

The decision to choose the type of the blades needs to be individualized. It depends on the patient's oral anatomical status, as well as personal preference and experiences.

The unpredictability of different types of patients that may come in to the operating room, emergency room, ambulance or other off-site operating room does pose an issue for medical practitioners. If a different blade shape is needed, due to different need of incoming patients or some unexpected airway management issues arising, the doctors or medical personnel must proceed to switch the blades or change to an alternative instrument with different maneuvering requirement, all done within a relatively short amount of time. Commonly, doctors and nurses will prepare, ahead of time, that both type of blades with varying sizes are available and in good working condition. Consequently, there exists a need to have a 2-blade combination laryngoscope that provides the flexibility, ease and simplicity to cope with the physical conditions of patients in need of endotracheal intubation.

In addition, the traditional handle portion of a laryngoscope consists of a round cylindrical tube that does not have effective ergonomical design to provide secure holding or better lifting power. Present invention's "pistol grip" handle design serves to provide a more stable, secure and efficient grip to the handle and thus greatly enhanced the safety and effectiveness of laryngoscopy procedures.

SUMMARY OF THE INVENTION

A laryngoscope consists of a combination of a straight blade and a curved blade on a single unit, allowing easy selection of which blade for use by the medical practitioner.

The two blades are connected to the handle by hinges and are foldable into a stored position by two grooves on the two opposite sides of the handle.

The two hinges can be made on the same end of the handle, or they can be made on the opposite ends of the handle. Each of the blades attached to the hinge will be made to be detachable and exchangeable, so that the blades can be changed to a different type of different size(s), depending on the practice needs.

Instead of smooth and straight cylindrical handle body, some indented gripping impression pattern is made to the outer surface of said handle, mimicking the pattern of a pistol's grip pattern, providing more secure gripping and better lifting power for medical practitioners, when the procedure of endotracheal intubation needs to be performed.

Inside the handle, a battery compartment is made to accommodate a battery of appropriate size and voltage, some needed accessories (such as wires and microprocessor, etc), so that there is power to drive optional lights (LED or other types) that may be put on the two ends of the handle, enabling better illumination effect at time of intubation.

DESCRIPTION OF THE DRAWINGS

The accompanying drawings, which are incorporated in and constitute a part of this specification, illustrate the preferred embodiments of the invention and together with the description, serve to explain the principles of the invention.

A brief description of the drawings is as follows.

DETAILED DESCRIPTION OF THE PREFERRED EMBODIMENT

Figure 1:
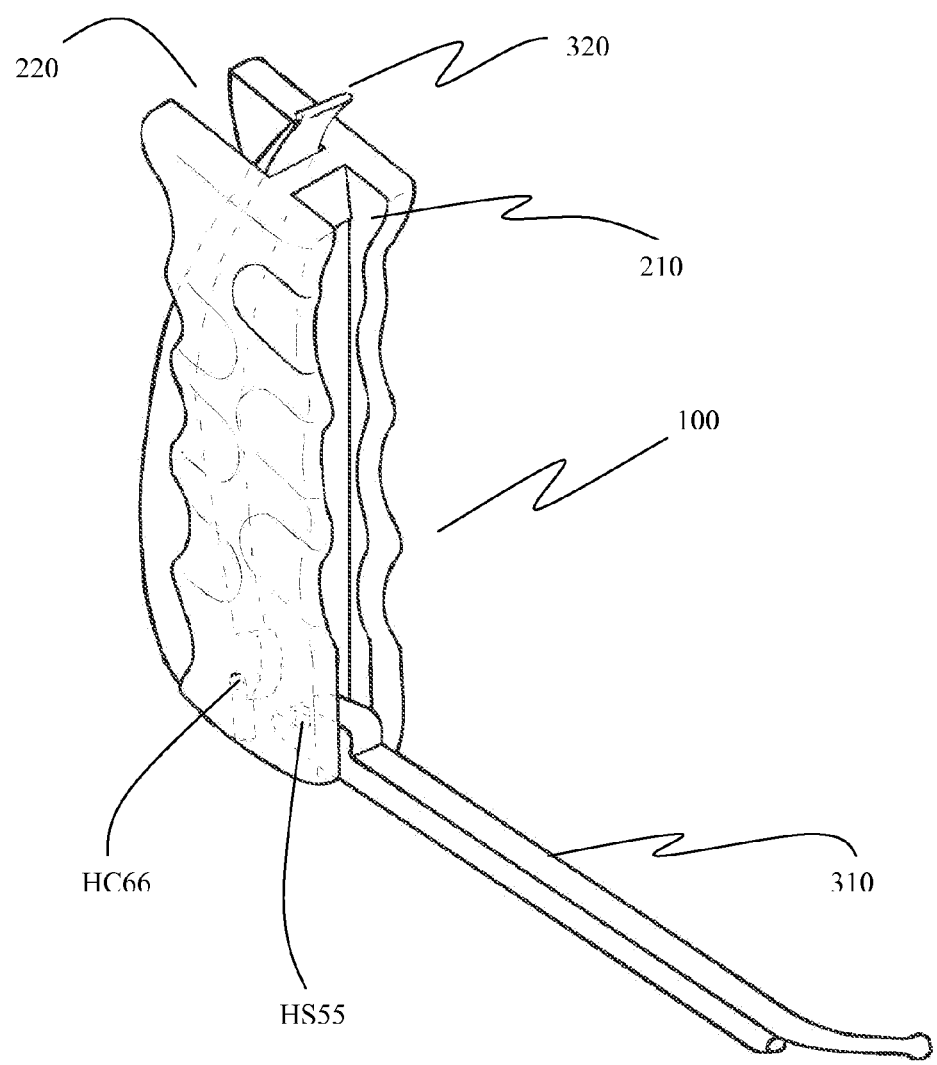
FIG. 1 shows the perspective view of the laryngoscope of present invention with the straight blade unfolded and the curved bladed folded into the corresponding groove. The two hinge connections for the curved and straight blades are made at the same end of the handle.

FIG. 1 shows the perspective view of a laryngoscope of present application, where the first groove 210 of a handle 100 is shown, having a straight blade 310 unfolded out from the first groove 210 along the first side of said handle 100.

The straight blade 310 is connected to said handle 100 with a hinge HS55.

FIG. 1 also shows another curved blade 320 with hinge connection HC66, near the same end as the hinge connection HS55 to the straight blade 310, which is folded into a second groove 220 on the opposite side of the handle 100.

The two hinge connections are made on the same end of the handle 100, as shown in FIG. 1.

Figure 2:
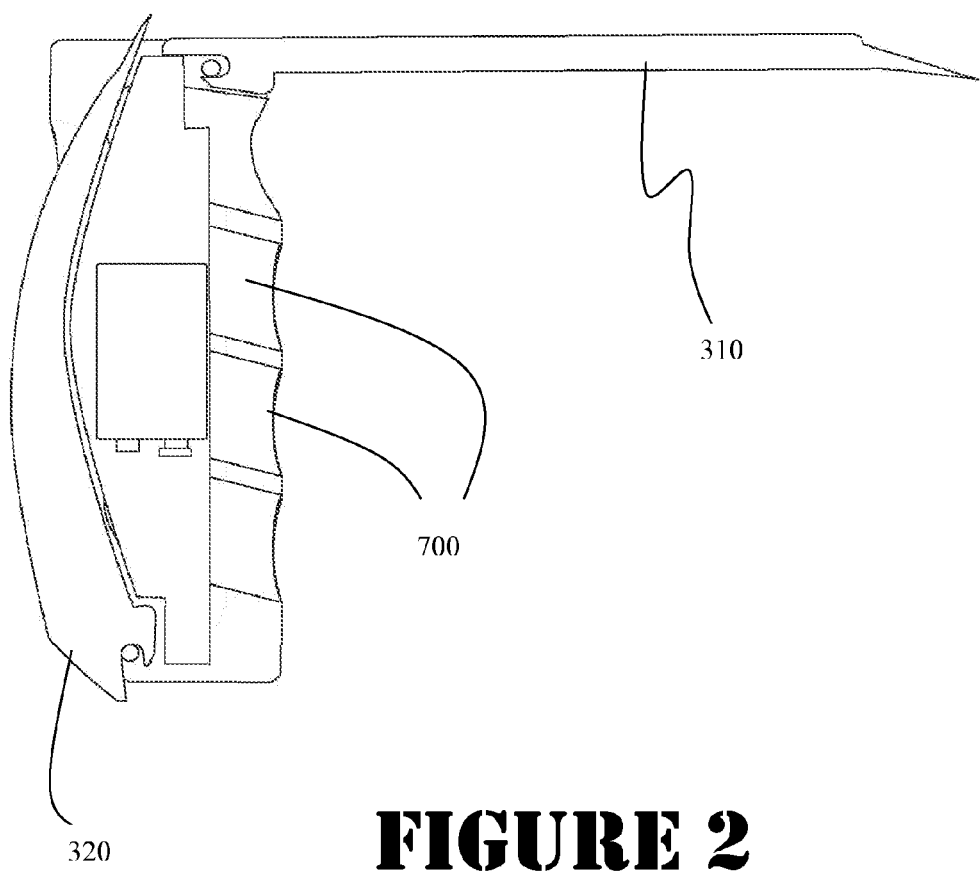
FIG. 2 shows the side view of the laryngoscope, with the grip impression pattern on the outside surface.

FIG. 2 shows that the hinge connection HS55 for straight blade 310 can be on the other end of the handle 100, in an alternative implementation.

Figure 3:
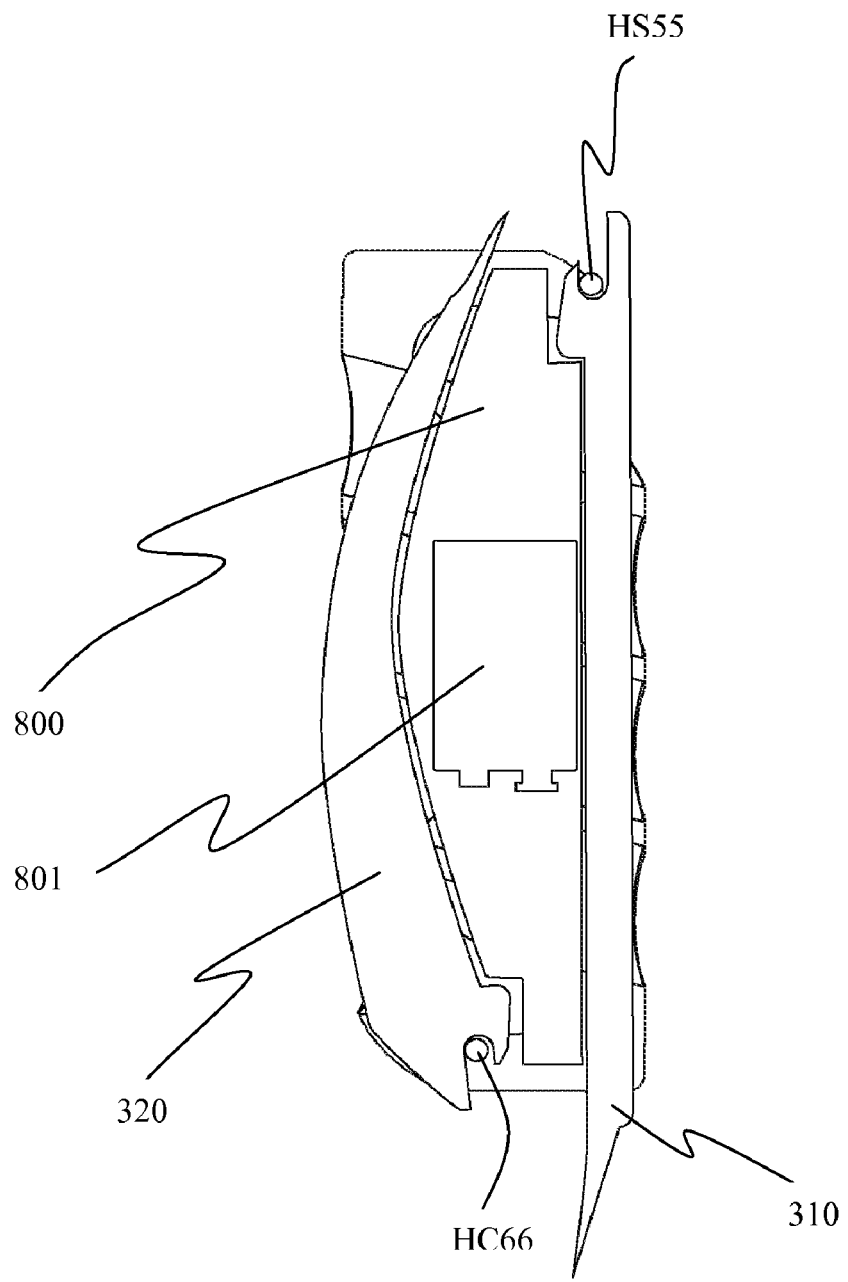
FIG. 3 shows the curved and straight blades' hinge connection at two opposite ends of the handle.

FIG. 3 shows the straight blade 310 and curved blade 320 being stored (folded) in its corresponding grooves 210/220, having respective hinge connections HS55 and HC66 located on the two opposite ends of said handle 100.

The hinges HC66 and HS55 are made to be detachable with the respective blades (straight/curved, 310/320), so that blades of different sizes/shapes can be used and exchanged dynamically by the medical practitioners.

Figure 4B:
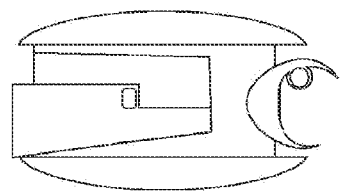
FIG. 4B shows the top profile view of the handle portion with two blades, along the A-A line indicated in FIG. 4A.
Figure 4A:
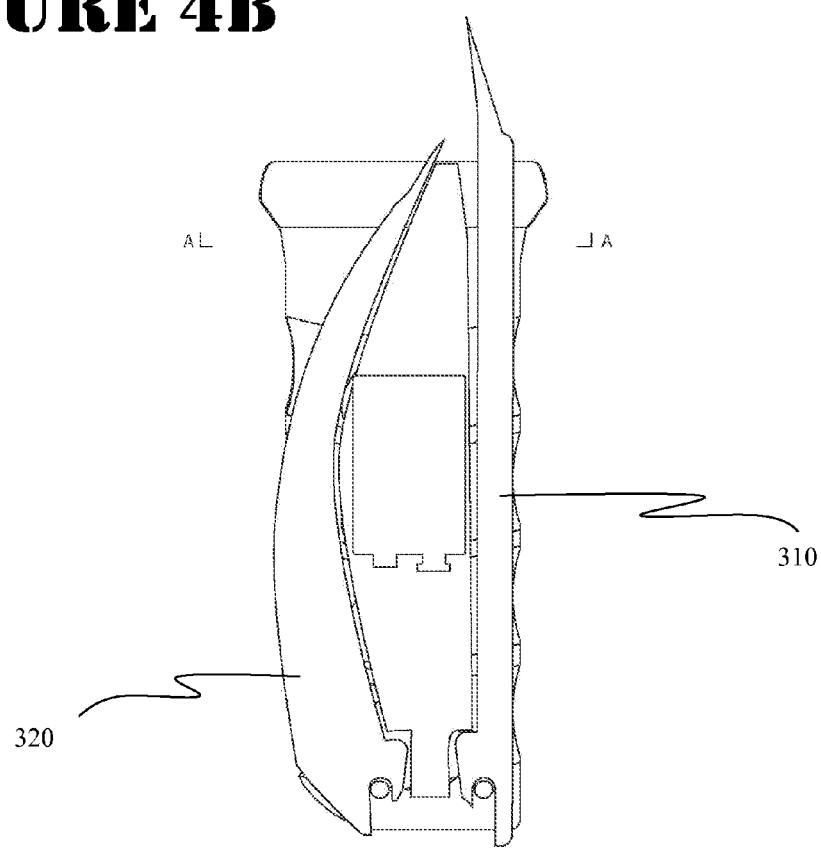
FIG. 4A shows the two hinge connections at the same end of the handle, having both blades folded. An internal battery compartment is shown, within the body of the handle portion.

FIG. 4A shows the straight blade 310 and curved blade 320 being stored (folded) in its corresponding grooves 210/220, having respective hinge connections HS55 and HC66 located on the same end, but opposite sides, of said handle 100.

FIG. 4B shows the top profile view of the laryngoscope along the line of A-A, as indicated in FIG. 4A, when the handle 100 is turned 90 degrees. Both straight blade 310 and curved blade 320 are folded into the respective grooves 210 and 220, on the same end of the handle 100.

The grooves 210 and 220 shown herein are shorter than the length of the straight blade 310 or curved blade 320, so that there will be some protruding tip from either straight blade 310 or curved blade 320, when they are folded into the grooves.

An internal compartment space 800 is made, inside the body of handle 100, for receiving a battery 801, providing the power to optional LED lighting, or other type of lighting, that can be added to the two ends of said handle 100.

Along the outside surface of handle 100, the gentle grip impression pattern 700 is made, generally resembling certain "pistol grip" pattern, so that there is more effective finger-holding contact area between the hand and the handle 100, providing a more stable and secure holding and handling by medical practitioners.

What is claimed is:

1. A laryngoscope with 2 selectable straight and curved blades, comprising:
    a. a handle having two grooves formed on the two opposite sides and along the length of said handle;
    b. a straight blade that can be received into a first groove formed on the first side of said handle, said straight blade is hingeably connected to a first end of said handle;
    c. a curved blade that can be received into a second groove formed on the second side of said handle, said curved blade is hingeably connected to said first end of said handle; and,
    d. said handle contains gripping impression pattern along its outer surface and is generally fitting to a person's fingers for easy and secure gripping/holding.

2. The laryngoscope of claim 1, wherein the connection between the blade and the hinge can be detached, allowing exchange of blades to different sizes/shapes to happen dynamically.

3. The laryngoscope of claim 2, wherein a battery compartment is built inside the body of said handle to accommodate a battery source, wires and microprocessor, to power light sources located at the two ends of said handle.

4. A laryngoscope with 2 selectable straight and curved blades, comprising:
    a. a handle having two grooves formed on the two opposite sides and along the length of said handle;
    b. a straight blade that can be received into a first groove formed on the first side of said handle, said straight blade is hingeably connected to the first end of said handle;
    c. a curved blade that can be received into a second groove formed on the second side of said handle, said curved blade is hingeably connected to a second end of said handle; and,
    d. said handle contains gripping impression pattern along its outer surface and is generally fitting to a person's fingers for easy and secure gripping/holding.

5. The laryngoscope of claim 4, wherein the connection between the blade and the hinge can be detached, allowing exchange of blades of different sizes/shapes to happen dynamically.

6. The laryngoscope of claim 5, wherein a battery compartment is built inside the body of said handle to accommodate a battery source, wires and microprocessor, to power light sources located at the two ends of said handle.

\* \* \* \* \*